(12) United States Patent
Izawa et al.

(10) Patent No.: US 9,434,706 B2
(45) Date of Patent: *Sep. 6, 2016

(54) 1,4-BUTANEDIOL-CONTAINING COMPOSITION

(71) Applicant: MITSUBISHI CHEMICAL CORPORATION, Chiyoda-ku (JP)

(72) Inventors: Yusuke Izawa, Mie (JP); Masaru Utsunomiya, Tokyo (JP); Norikazu Konishi, Mie (JP); Kouta Tanaka, Mie (JP); Takayuki Suzuki, Mie (JP); Shinichirou Matsuzono, Mie (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/150,174

(22) Filed: Jan. 8, 2014

(65) Prior Publication Data

US 2014/0187740 A1 Jul. 3, 2014

Related U.S. Application Data

(63) Continuation of application No. PCT/JP2012/067010, filed on Jul. 3, 2012.

(30) Foreign Application Priority Data

Jul. 8, 2011 (JP) .................... 2011-151716
Nov. 2, 2011 (JP) .................... 2011-241572

(51) Int. Cl.

| C07C 31/20 | (2006.01) |
|---|---|
| C07D 307/08 | (2006.01) |
| C07C 29/94 | (2006.01) |
| C08G 63/183 | (2006.01) |
| C08G 63/78 | (2006.01) |
| C07D 307/02 | (2006.01) |
| C08K 5/20 | (2006.01) |

(52) U.S. Cl.
CPC ............ *C07D 307/08* (2013.01); *C07C 29/94* (2013.01); *C08G 63/183* (2013.01); *C08G 63/78* (2013.01); *C08K 5/20* (2013.01)

(58) Field of Classification Search
CPC ... C07C 29/94; C07C 31/207; C07D 307/08; C08G 63/183; C08G 63/78; C08K 5/20
USPC .......................... 568/617; 549/509
See application file for complete search history.

(56) References Cited

U.S. PATENT DOCUMENTS

| 4,511,708 A | 4/1985 | Kasuga et al. |
|---|---|---|
| 5,319,111 A | 6/1994 | Zimmermann et al. |
| 5,397,439 A | 3/1995 | Kandori et al. |
| 2006/0122365 A1 | 6/2006 | Pinkos et al. |
| 2008/0081886 A1 | 4/2008 | Yamamoto et al. |
| 2009/0099392 A1 | 4/2009 | Hino et al. |
| 2009/0171037 A1 | 7/2009 | Aoshima et al. |

FOREIGN PATENT DOCUMENTS

| JP | 52-007909 | 1/1977 |
|---|---|---|
| JP | 59-140223 | 8/1984 |
| JP | 62-4174 | 1/1987 |
| JP | 6-234679 A | 8/1994 |
| JP | 07-010981 | 1/1995 |
| JP | 9-59191 A | 3/1997 |
| JP | 10-265418 A | 10/1998 |
| JP | 2001-114884 | 4/2001 |
| JP | 2005-350659 | 12/2005 |
| JP | 2006-503050 | 1/2006 |
| JP | 2008-101143 A | 5/2008 |
| JP | 2009-77719 | 4/2009 |
| JP | 4582228 B2 | 11/2010 |
| WO | 2004/026853 | 4/2004 |

OTHER PUBLICATIONS 1,4-Butanediol Tech Data Millipore Web Site 2015.*
Office Action issued on May 29, 2015 in European Patent Application No. 12 811 651.4.
U.S. Appl. No. 14/560,714, filed Dec. 4, 2014, Utsunomiya, et al.
International Search Report issued Oct. 2, 2012 in PCT/JP2012/067010 filed Jul. 3, 2012.
Extended European Search Report issued on Jun. 18, 2014 in the corresponding European Application No. 12811651.4.
U.S. Appl. No. 14/147,885, filed Jan. 6, 2014, Izawa, et al.
Combined Chinese Office Action and Search Report issued Oct. 31, 2014 in Patent Application No. 201280033504.2 (with English Translation and English Translation of Category of Cited Documents).
Office Action issued Aug. 24, 2015 in Chinese Patent Application No. 201280033504.2 (with English language translation).
Office Action issued Jan. 18, 2016 in European Patent Application No. 12 811 651.4.
Combined Taiwanese Office Action and Search Report issued Dec. 23, 2015 in Patent Application No. 101124189 (with English language translation).
Japanese Office Action issued Jan. 26, 2016 in Patent Application No. 2012-152803 (with unedited computer generated English translation).
Office Action as received in the corresponding Chinese Patent Application No. 201280033504.2 dated May 5, 2016 w/English Translation.

\* cited by examiner

*Primary Examiner* — Ling Choi
*Assistant Examiner* — Gennadiy Mesh
(74) *Attorney, Agent, or Firm* — Oblon, McClelland, Maier & Neustadt, L.L.P.

(57) ABSTRACT

A 1,4-butanediol (1,4BG)-containing composition having high thermal stability, and having a concentration of 1,4-butanediol of 99.00% by weight or more and not more than 99.99% by weight and 2-pyrrolidone or N-methylpyrrolidone in a concentration, as converted into a nitrogen atom, of from 1.0 to 25 ppm by weight.

3 Claims, No Drawings

1,4-BUTANEDIOL-CONTAINING COMPOSITION

TECHNICAL FIELD

The present invention relates to a 1,4-butanediol-containing composition.

BACKGROUND ART

It is known that 1,4-butanediol (hereinafter sometimes abbreviated as "1,4BG") is an extremely useful substance which is used as a raw material of various solvents or derivatives. A variety of methods for industrially producing 1,4BG have hitherto been developed. For example, there are exemplified a method in which butadiene is used as a raw material, an acetoxylation reaction is conducted by using the raw material butadiene, acetic acid, and oxygen to obtain diacetoxybutene that is an intermediate, and the diacetoxybutene is hydrogenated and hydrolyzed to obtain 1,4BG (Patent Document 1); a method in which maleic acid, succinic acid, maleic anhydride, and/or fumaric acid is used as a raw material, and such a raw material is hydrogenated to obtain a crude hydrogenation product containing 1,4BG (Patent Document 2); a method in which butynediol obtained by bringing acetylene as a raw material into contact with a formaldehyde aqueous solution is hydrogenated to produce 1,4BG (Patent Document 3); and the like.

Though tetrahydrofuran (hereinafter sometimes abbreviated as "THF") that is a derivative obtained from 1,4BG as a raw material is in general used as a solvent, it is also used as a raw material of polyether polyols (specifically polytetramethylene ether glycol). As for a method for producing THF from 1,4BG, Patent Document 4 describes that in a method for continuously producing THF by allowing a reaction mixture containing 1,4BG to react over a heteropolyacid catalyst, by allowing the reaction mixture to contain 2-(4-hydroxybutoxy)-tetrahydrofuran and less than 1 ppm of a basic nitrogen component, the life of the heteropolyacid catalyst can be made long. In addition, polybutylene terephthalate (hereinafter sometimes abbreviated as "PBT") is other derivative obtained from 1,4BG as a raw material. Patent Document 5 describes a method for producing PBT in which in the esterification reaction, in order to avoid loss of 1,4BG as a raw material due to side reaction to produce THF, a reaction condition (e.g., a concentration of catalyst raw material, a reaction pressure, a ratio of terephthalic acid and 1,4BG, etc.) is controlled.

BACKGROUND ART DOCUMENT

Patent Document

Patent Document 1: JP-A-52-7909
Patent Document 2: Japanese Patent No. 2930141
Patent Document 3: JP-B-62-4174
Patent Document 4: JP-T-2006-503050
Patent Document 5: JP-A-2005-350659

SUMMARY OF INVENTION

Problem that Invention is to Solve 1,4BG obtained by the methods described in the foregoing Patent Documents 1 to 3 is crude 1,4BG with a low purity, which contains unreacted raw materials, by-products, and impurities generated from the catalysts used in the production process, or the like. Therefore, in order to use 1,4BG as the raw material for derivatives described in Patent Document 4 or Patent Document 5, in general, 1,4BG with a good quality is used after conducting purification such as distillation, etc. so as to meet the specs for the purpose of use of 1,4BG.

However, when the purified 1,4BG with a good quality is actually applied for the use, it has become clear that the thermal stability of 1,4BG whose quality is poor as compared with that immediately after obtaining through purification, in particular, on the occasion of using 1,4BG as a raw material of PBT (THF is generated in 1,4BG), is deteriorated.

In view of the foregoing problems, the present invention has been made, and an object thereof is to provide a 1,4-butanediol-containing composition having high thermal stability as compared with conventional 1,4BG.

Means for Solving Problem

In order to solve the foregoing problems, the present inventors made extensive and intensive investigations. As a result, it has been found that a minute amount of an acid content which cannot be removed by the conventional purification is present in 1,4BG obtained through purification, and it works as an acid catalyst; and therefore, under a supposition that a part of 1,4BG is converted into THF, among nitrogen-containing compounds which have hitherto been considered to be a cause of catalyst deterioration, when an amide which is small in influences against the catalyst deterioration at the time of production of derivatives following an increase of the pH on the occasion of bringing 1,4BG into contact with a base component such as an alkali metal, etc. is mixed within a specified concentration range, astonishingly, not only the catalyst deterioration can be inhibited, but the conversion of 1,4BG into THF can be suppressed, and as a result, the thermal stability can be significantly improved, leading to accomplishment of the present invention.

The present invention has been achieved on the basis of such knowledge, and its gist includes the following [1] to [4].

[1]

A 1,4-butanediol-containing composition having a concentration of 1,4-butanediol of 99.00% by weight or more and not more than 99.99% by weight and containing an amide compound in a concentration, as converted into a nitrogen atom, of from 1.0 to 50 ppm by weight.

[2]

The 1,4-butanediol-containing composition as described in [1], a pH is 5.0 or more and not more than 7.9.

[3]

A method for producing a polyester, comprising:

conducting a polycondensation reaction of 1,4-butanediol with at least one of a dicarboxylic acid and a dicarboxylic acid ester, wherein a 1,4-butanediol-containing composition having a concentration of 1,4-butanediol of 99.00% by weight or more and not more than 99.99% by weight and containing an amide compound in a concentration, as converted into a nitrogen atom, of from 1.0 to 50 ppm by weight is used as a raw material.

[4]

A method for producing tetrahydrofuran, comprising:

conducting a dehydration cyclization reaction of 1,4-butanediol by using, as a raw material, a 1,4-butanediolcontaining composition having a concentration of 1,4-butanediol of 99.00% by weight or more and not more than 99.99% by weight and containing an amide compound in a concentration, as converted into a nitrogen atom, of from 1.0 to 50 ppm by weight within a reactor in a presence of an acid catalyst having a pKa value of not more than 4, so as to obtain tetrahydrofuran.

Effects of Invention

The 1,4-butanediol-containing composition of the present invention is high in terms of thermal stability, and even when it is used as a raw material of derivatives, coloration or catalyst poisoning of post-steps can be suppressed.

MODE FOR CARRYING OUT INVENTION

The present invention is hereunder described in more detail.

It is possible to obtain 1,4BG which is contained in the 1,4-butanediol-containing composition of the present invention by production methods which have hitherto been known. For example, there are included 1,4BG obtained by conducting an acetoxylation reaction using raw material butadiene, acetic acid, and oxygen to obtain diacetoxybutene that is an intermediate and hydrogenating and hydrolyzing the diacetoxybutene; 1,4BG obtained by using maleic acid, succinic acid, maleic anhydride, and/or fumaric acid as a raw material and hydrogenating such a raw material; crude 1,4BG obtained by hydrogenating butynediol obtained by bringing acetylene as a raw material into contact with a formaldehyde aqueous solution; 1,4BG obtained through oxidation of propylene; 1,4BG obtained by hydrogenating succinic acid obtained by a fermentation method; 1,4BG obtained by means of direct fermentation from a biomass such as a sugar, etc.; and the like.

A concentration of 1,4BG in the 1,4-butanediol-containing composition of the present invention is 99.00% by weight or more and not more than 99.99% by weight, preferably 99.20% by weight or more and not more than 99.97% by weight, and more preferably 99.50% by weight or more and not more than 99.95% weight. There is a concern that when the concentration of 1,4BG is higher, the purification cost becomes higher, whereas when the concentration of 1,4BG is lower, a by-product becomes more liable to be formed to cause coloration at the time of polyester production or the like.

The 1,4-butanediol-containing composition of the present invention is required to contain an amide compound. In the 1,4-butanediol-containing composition of the present invention, though the thermal stability becomes high due to the amide compound, the reasons for this are not always elucidated yet. However, it may be supposed that a THF formation promoting substance of an infinitesimal amount not more than a detection limit is present in 1,4-butanediol, and in view of the fact that the amide compound makes the promoting substance nonpoisonous, the thermal stability can be enhanced. Among amide compounds, it is preferable to contain a carboxylic acid amide. A primary amide, a secondary amide, and a tertiary amide can be used as the carboxylic acid amide. An N-alkyl-substituted amide, an N-alkenyl-substituted amide, an N-aryl-substituted amide, and the like are used in the N-substituted substituent number in the range of from 0 to 2. In addition, a hetero atom may be contained in the substituent, and the plural substituents may be the same as or different from each other. On the other hand, examples of the substituent on the carbonyl side include a hydrogen atom, an alkyl group, an alkenyl group, an aryl group, and the like. In addition, the above-described substituents may be connected to each other to form a ring. An alkyl group is preferable as the substituent on the carbonyl side from the viewpoint that when the 1,4-butanediol-containing composition of the present invention is treated within a distillation column, side reaction, decomposition, or the like can be inhibited.

In addition, for the reasons that the carboxylic acid amide is always coexistent together with 1,4-butanediol, thereby continuously revealing a thermal stabilization effect, and when the 1,4-butanediol-containing composition is treated within a distillation column, staining on the column bottom or the like is avoided, a compound having a boiling point under atmospheric pressure of from 160 to 300° C. is preferably used. The boiling point is more preferably from 165 to 280° C., and especially preferably from 170 to 250° C. In the case where the boiling point is higher than the foregoing range, the adjustment of a nitrogen concentration in the 1,4-butanediol-containing composition of the present invention becomes difficult, whereas in the case where the boiling point is too low, in addition to the fact that the adjustment of the nitrogen concentration is difficult, a hindrance of driving operation is caused.

In the present invention, as specific examples of the amide compound, there are preferably exemplified acetamide as the primary amide; N-methylacetamide and N-ethylacetamide as the secondary amide; an amide having a chain skeleton, such as N,N-dimethylacetamide, etc., and an aromatic amide such as benzamide, etc., as the tertiary amide; 2-pyrrolidone as the secondary amide; and a cyclic amide such as N-methylpyrrolidone, N-ethylpyrrolidone, N-vinylpyrrolidone, 2-piperidone, N-methylpiperidone, etc., as the tertiary amide. There are more preferably exemplified acetamide, N-methylacetamide, 2-pyrrolidone, and N-methylpyrrolidone, with acetamide, 2-pyrrolidone, or N-methylpyrrolidone being especially preferable. In addition, the amide which is contained in the 1,4-butanediol-containing composition of the present invention may be a single kind or two or more kinds thereof.

The 1,4-butanediol-containing composition of the present invention is characterized by containing the above-described amide compound in a concentration, as converted into a nitrogen atom, of from 1.0 to 50 ppm by weight. It is possible to obtain the 1,4-butanediol-containing composition of the above-described concentration range by directly adding the amide compound to commercially available 1,4BG, 1,4BG obtained by the above-described conventionally known production method of 1,4BG, or 1,4BG after purifying the 1,4BG, followed by preparation. Furthermore, it is also possible to obtain the 1,4-butanediol-containing composition by adding the amide compound to the raw material by the above-described conventionally known production method of 1,4BG or on the way of a process of production step of such 1,4BG, followed by preparation.

For example, in the case of obtaining the 1,4-butanediol-containing composition by conducting an acetoxylation reaction using raw material butadiene, acetic acid, and oxygen to obtain diacetoxybutene that is an intermediate and hydrolyzing the diacetoxybutene and water, the diacetoxybutene may be produced by introducing the amide into a diacetoxylation reactor, or 1,4-diacetoxybutane containing a nitrogen content may be produced by introducing the amide in a subsequent hydrogenation step. In addition, a mixture containing 1,4-butanediol, water, and 1-acetoxy-4-hydroxybutane may be obtained by introducing the amide in a hydrolysis step. In addition, the amide may also be introduced into a distillation column for obtaining a purified product 1,4BG having a high purity, which has been separated from such a mixture, or in a hydrogenation step for removing impurities. In addition, for example, in the case of obtaining a hydrogenation reaction mixture containing 1,4BG obtained by using maleic acid, succinic acid, maleic anhydride, and/or fumaric acid as a raw material and hydrogenating such a raw material, γ-butyrolactone, and tetrahydrofuran, the amide may be introduced into this hydrogenation reaction mixture. Incidentally, in the case of adding the amide on the way of a process of such a production step, as for its addition amount, an amount of the amide larger than 50 ppm by weight is allowed to be added. That is, the addition amount of the amide may be adjusted such that the amide is contained in a concentration, as converted into a nitrogen atom, of from 1.0 to 50 ppm by weight in the finally obtained 1,4-butanediol-containing composition.

In the present invention, when the amide compound is added in the 1,4-butanediol production process, there are no particular limitations in terms of its boiling point and concentration, and hence, the amide compound is allowed to be added in any state of gas, liquid, or solid. In addition, the amide compound is also allowed to be added upon being dissolved in the raw material or product, a solvent, water, or the like. The content of the amide compound which is contained for other purpose may also be adjusted in advance.

In addition, the amide compound is also allowed to be added directly to 1,4-butanediol having a purity of 99% or more as obtained by purifying 1,4BG produced by the above-described conventional method, such that its content is 1.0 ppm by weight or more and not more than 50 ppm by weight. In that case, it is naturally necessary to add a minute amount of the amide compound such that the purity of the product 1,4-butanediol after the addition of the amide is 99% by weight or more and not more than 99.99% by weight as specified in the present invention.

The concentration, as converted into a nitrogen atom, of the amide compound contained in the 1,4-butanediol-containing composition of the present invention is 1.0 ppm by weight or more and not more than 50 ppm by weight, preferably 3.0 ppm by weight or more and not more than 40 ppm by weight, and more preferably 10 ppm by weight or more and not more than 25 ppm by weight. In the case where the concentration as converted into a nitrogen atom is higher than the foregoing range, coloration or catalyst poisoning on the occasion of deriving into other products such as a polyester, etc. becomes large. In addition, in the case where the concentration as converted into a nitrogen atom is too low, an affect for improving the quality such as thermal stability, etc. is lowered.

In addition, a pH of the 1,4-butanediol-containing composition of the present invention is preferably 5.0 or more and not more than 7.9, more preferably 5.5 or more and not more than 7.0, and especially preferably 5.7 or more and not more than 6.9. In the case where the pH is higher than the foregoing range, coloration or catalyst poisoning on the occasion of deriving into other products such as a polyester, etc. tends to become large. In addition, in the case where the pH is too low, an affect for improving the thermal stability to be brought due to the fact of containing the amide compound tends to be lowered.

The 1,4-butanediol-containing composition of the present invention is preferable for the use of production of a polyester such as PBT, polybutylene succinate, etc., γ-butyrolactone, or tetrahydrofuran.

For example, in the case of producing a polyester by using the 1,4-butanediol-containing composition of the present invention as a raw material, in a method for producing a polyester by a polycondensation reaction of 1,4-butanediol with at least one of a dicarboxylic acid and a dicarboxylic acid ester, the 1,4-butanediol-containing composition is preferably one having a concentration of 1,4-butanediol of 99.0% by weight or more and not more than 99.99% by weight and a concentration, as converted into a nitrogen atom, of the amide compound of from 1.0 to 50 ppm by weight.

Incidentally, among polyesters, on the occasion of producing PBT, it is more preferable to use the 1,4-butanediol-containing composition of the present invention, and as its production method, a known production method can be adopted. For example, the known production method of PBT is roughly classified into a so-called direct polymerization method using terephthalic acid as a main raw material; and an ester interchange method using a terephthalic acid dialkyl ester as a main raw material. In all of these cases, 1,4-butanediol is easily converted into tetrahydrofuran during the polymerization reaction, and a production method of PBT with a low degree of conversion into tetrahydrofuran is demanded. Though there is such a difference that in the direct polymerization, water is formed in the initial esterification reaction, whereas in the ester interchange method, an alcohol is formed in the initial ester interchange reaction, the direct polymerization method is preferable from the viewpoints of stable availability of a raw material, easiness of treatment of a distillate, height of basic unit of a raw material, and improving effects according to the present invention. The 1,4-butanediol-containing composition having high thermal stability according to the present invention is very effective as the production method of PBT with a low degree of conversion into tetrahydrofuran and a small loss of the raw material.

Incidentally, in the production of PBT, in order to distil a light-boiling component in the production process, in the present invention, the amide is preferably a compound having a boiling point under atmospheric pressure of from 160 to 300° C.

In addition, for example, as a method for producing THF by using the 1,4-butanediol-containing composition of the present invention, a known production method for subjecting 1,4BG to a dehydration cyclization reaction into THF in the presence of an acid catalyst can be applied. In the present invention, as a reactor for conducting the dehydration cyclization reaction, a fixed bed reactor filled with a solid catalyst such as a cation exchange resin, etc., a suspended bed reactor using a solid catalyst, or a vessel type or tubular reactor using a homogenous acid catalyst capable of being dissolved in the raw material can be used. In addition, though it may be possible to obtain THF by discharging a solution containing THF and by-product water in a liquid phase part within a reactor from the reactor, followed by purification in post-steps such as a distillation column, etc., it is also possible to extract a part or the whole of THF as a gas containing formed THF and by-product water from a vapor phase of the reactor.

An arbitrary acid catalyst having a pKa value of not more than 4 can be used as the acid catalyst. However, the acid catalyst is preferably sulfonic acid, a cation exchange resin, a heteropolyacid, phosphoric acid, or the like, more preferably a metal-free organic acid or phosphoric acid, and especially preferably an organic sulfonic acid. Specifically, examples thereof include an aromatic sulfonic acid derivative such as p-toluenesulfonic acid, benzenesulfonic acid, o-toluenesulfonic acid, m-toluenesulfonic acid, etc.; a chain aliphatic sulfonic acid derivative such as butanesulfonic acid, hexanesulfonic acid, octanesulfonic acid, nonanesulfonic acid, etc.; and the like. These are allowed to have other substituent than sulfonic acid in a carbon skeleton. These acid catalysts may be used solely or in admixture of two or more kinds thereof. p-Toluenesulfonic acid is especially preferably used as the acid catalyst.

In general, such an acid catalyst is neutralized and deteriorated in the presence of a basic component. In order to increase the thermal stability of 1,4-butanediol, a method for adding an inorganic base, or the like is known. However, when this method is adopted, the acid catalyst is deteriorated. On the other hand, since the 1,4-butanediol-containing composition having high thermal stability according to the present invention is not high in basicity, it does not accelerate the deterioration of the acid catalyst.

In addition, when tetrahydrofuran is produced by using the 1,4-butanediol-containing composition of the present invention, the amount of 2-(4-hydroxybutoxy)tetrahydrofuran is reduced in the presence of by-product water within the reactor, whereby the production of a by-product solid can be effectively inhibited.

In general, a derivative of 1,4BG, such as THF, PBT, etc., is produced by using an acid catalyst. For that reason, it is desirable to use a 1,4BG composition having a pH kept at not more than 7 and also having high thermal stability.

EXAMPLES

The present invention is hereunder described in more detail by reference to the following Examples, but it should not be construed that the present invention is limited to these Examples so long as the gist of the present invention is not deviated.

Incidentally, in the following Examples, the analysis of 1,4-butanediol and tetrahydrofuran was conducted by means of gas chromatography, and 1,4-butanediol was calculated by means of correction with the water content by the Karl Fisher's method (measured by "CA-21", manufactured by Mitsubishi Chemical Corporation) according to the corrected area percentage method. Tetrahydrofuran was calculated according to the internal standard method (internal standard: n-octadecane). The concentration, as converted into a nitrogen atom, of a nitrogen-containing compound was calculated from the amount of an added amine.

As for only synthesis examples of PBT (Examples 10 to 12 and Comparative Example 4), various analyses were carried out by the following methods. As for the analysis of tetrahydrofuran, an organic component was determined by means of gas chromatography according to the corrected area percentage method and calculated by means of correction with the water content by the Karl Fisher's method (measured by "CA-200", manufactured by Mitsubishi Chemical Corporation). A formation amount of tetrahydrofuran was expressed in terms of % by mole relative to terephthalic acid and defined as a degree of conversion. An intrinsic viscosity (IV) of PBT was determined by using an Ubbelohde viscometer according to the following procedures. That is, a mixed solvent of phenol/tetrachloroethane (mass ratio: 1/1) was used, and the falling number of seconds of each of a polymer solution having a concentration of 1.0 g/dL and only a solvent was measured and determined according to the following equation.

$$IV=((1+4K_H\eta_{sp})^{0.5}-1)/(2K_HC)$$

Here, $\eta_{sp}=(\eta/\eta_0)-1$; $\eta$ represents the falling number of seconds of the polymer solution; $\eta_0$ represents the falling number of seconds of the solvent; C represents a concentration of the polymer solution (g/dL); and $K_H$ represents a constant of Huggins. 0.33 was adopted as $K_H$.

As for the color tone of the PBT pellets, a pellet-shaped polyester was filled in a columnar cell for solid measurement having an inner diameter of 30 mm and a depth of 12 mm, and a b value according to the color coordinates in the Hunter's color difference equation in the Lab display system described in Reference Example 1 of JIS Z8730 by using a photoelectric color difference meter Z300A (manufactured by Nippon Denshoku Industries Co., Ltd.) were measured at four points by the reflection method while rotating the measurement cell at intervals of 90° and determined as a simple average value.

Example 1

1.4 mg of acetamide was added to 25.0 g of commercially available 1,4-butanediol (manufactured by Mitsubishi Chemical Corporation), thereby preparing a 1,4-butanediol-containing composition containing acetamide in a concentration, as converted into a nitrogen atom, of 5.0 ppm by weight (1,4BG concentration: 99.6% by weight). As a result of measuring a pH, it was found to be 5.6.

This composition was transferred into a 100-mL stainless steel autoclave, and after carrying out nitrogen substitution within the container, the resulting composition was heated at 242° C. for one hour. After cooling the autoclave, the 1,4-butanediol-containing composition was taken out, and the generation amount of tetrahydrofuran was analyzed. As a result, it was found to be 800 ppm by weight. The results are shown in Table 1.

Example 2

Procedures exactly the same as those in Example 1 were carried out, except that in Example 1,2-pyrrolidone was used in a concentration, as converted into a nitrogen atom, of 1.2 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 2,998 ppm by weight. The results are shown in Table 1.

Example 3

Procedures exactly the same as those in Example 1 were carried out, except that in Example 1,2-pyrrolidone was used in a concentration, as converted into a nitrogen atom, of 5.0 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 2,180 ppm by weight. The results are shown in Table 1.

Example 4

Procedures exactly the same as those in Example 1 were carried out, except that in Example 1,2-pyrrolidone was used in a concentration, as converted into a nitrogen atom, of 21.0 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 978 ppm by weight. The results are shown in Table 1.

Example 5

Procedures exactly the same as those in Example 1 were carried out, except that in Example 1,2-pyrrolidone was used in a concentration, as converted into a nitrogen atom, of 50.0 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 2,109 ppm by weight. The results are shown in Table 1.

Example 6

Procedures exactly the same as those in Example 1 were carried out, except that in Example 1, N-methylpyrrolidone was used in a concentration, as converted into a nitrogen atom, of 1.2 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 4,020 ppm by weight. The results are shown in Table 1.

Example 7

Procedures exactly the same as those in Example 1 were carried out, except that in Example 1, N-methylpyrrolidone was used in a concentration, as converted into a nitrogen atom, of 5.0 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 1,300 ppm by weight. The results are shown in Table 1.

Example 8

Procedures exactly the same as those in Example 1 were carried out, except that in Example 1, N-methylpyrrolidone was used in a concentration, as converted into a nitrogen atom, of 21.0 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 704 ppm by weight. The results are shown in Table 1.

Example 9

Procedures exactly the same as those in Example 1 were carried out, except that in Example 1, N-methylpyrrolidone was used in a concentration, as converted into a nitrogen atom, of 50.0 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 1,335 ppm by weight. The results are shown in Table 1.

Comparative Example 1

Procedures exactly the same as those in Example 1 were carried out, except that in Example 1, the acetamide was not added, and the commercially available 1,4-butanediol was heated. The concentration, as converted into a nitrogen atom, of the amide in 1,4-butanediol before heating was not more than a detection limit. In addition, the pH was 5.5. As a result of analyzing the generation amount of tetrahydrofuran in the 1,4-butanediol after heating, it was found to be 6,800 ppm by weight. The results are shown in Table 1.

Comparative Example 2

Procedures exactly the same as those in Example 1 were carried out, except that in Example 1, N-methylpyrrolidone was used in a concentration, as converted into a nitrogen atom, of 0.5 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 12,507 ppm by weight. The results are shown in Table 1.

Comparative Example 3

Procedures exactly the same as those in Example 1 were carried out, except that in Example 1,2-pyrrolidone was used in a concentration, as converted into a nitrogen atom, of 0.1 ppm by weight in place of the acetamide. Incidentally, the pH of the 1,4-butanediol-containing composition before heating was 5.5. As a result of analyzing the generation amount of tetrahydrofuran in the 1,4-butanediol-containing composition after heating, it was found to be 7,773 ppm by weight. The results are shown in Table 1.

Example 10

Production of PBT

In a reactor equipped with a stirrer, a nitrogen-introducing inlet, a heating device, a thermometer, and an exhaust port for evacuation, 113 g of terephthalic acid, 184 g of a 1,4-butanediol-containing composition containing 2-pyrrolidone in a concentration, as converted into a nitrogen atom, of 4.0 ppm by weight (concentration of 1,4BG: 99.4% by weight, pH: 5.5), and 0.7 g of a solution in which 6% by weight of tetrabutyl titanate as a catalyst had been dissolved in advance were charged, and the inside of the system was made under a nitrogen atmosphere by means of nitrogen substitution under reduced pressure. After heating the inside of the system to 150° C. while stirring, the temperature was increased to 220° C. under atmospheric pressure over one hour, and an esterification reaction was conducted for an additional 2 hours while distilling formed water. Subsequently, 1.3 g of a 1,4-butanediol solution of 1% by weight of magnesium acetate tetrahydrate prepared by dissolving magnesium acetate tetrahydrate in water and further dissolving in 1,4BG (mass ratio of magnesium acetate tetrahydrate to water to 1,4-butanediol=1/2/97) was added. Subsequently, the temperature was increased to 245° C. over one hour, and the pressure was reduced to 0.07 kPa over 1.5 hours. A polycondensation reaction was conducted at the same degree of pressure reduction for 1.1 hours, and the reaction system was then returned to atmospheric pressure, thereby finishing the polycondensation. The obtained PBT was extracted as a strand from the bottom part of the reaction vessel and dipped in water at 10° C. The resulting strand was then cut using a cutter, thereby obtaining pellet-shaped PBT. A color-b expressing a degree of coloration of the obtained PBT was 2.2.

A time from start of the pressure reduction after adding magnesium acetate to finish of the polycondensation was defined as a polycondensation time, and an (intrinsic viscosity)/(polycondensation time) was defined as a polycondensation rate. The polycondensation rate was 0.37 dL/g/h. A degree of conversion into THF was expressed in terms of % by mole per charged terephthalic acid upon analysis of the amount of THF in a distillation liquid during the esterification reaction. The degree of conversion into THF was 63.7% by mole. The results are shown in Table 2.

Example 11

PBT was obtained by carrying out procedures exactly the same as those in Example 10, except that in Example 10, a 1,4-butanediol-containing composition containing 2-pyrrolidone in a concentration, as converted into a nitrogen atom, of 6.6 ppm by weight was used. As a result, the polycondensation rate was 0.37 dL/g/h. In addition, the color-b expressing a degree of coloration of the obtained PBT was 2.9. The results are shown in Table 2.

Example 12

PBT was obtained by carrying out procedures exactly the same as those in Example 10, except that in Example 10, a 1,4-butanediol-containing composition containing 2-pyrrolidone in a concentration, as converted into a nitrogen atom, of 20.2 ppm by weight was used. As a result, the polycondensation rate was 0.37 dL/g/h. In addition, the degree of conversion into THF was 64.6%. In addition, the color-b expressing a degree of coloration of the obtained PBT was 3.3. The results are shown in Table 2.

Comparative Example 4

Procedures exactly the same as those in Example 10 were carried out to obtain PBT, except that in Example 10, the 1,4-butanediol-containing composition was changed to commercially available 1,4BG not containing 2-pyrrolidone (not more than a detection limit). As a result, the polycondensation rate was 0.36 dL/g/h. In addition, the degree of conversion into THF was 78.6%. The results are shown in Table 2.

Reference Example 1

Production of THF

In a 9-mL glass vial, 2.0 g of commercially available 1,4-butanediol (manufactured by Mitsubishi Chemical Corporation) and 1.2 mg of p-toluenesulfonic acid monohydrate were added and stirred at 60° C. for 2 hours.

As a result of analyzing the content of tetrahydrofuran after heating, it was found to be 1,003 ppm by weight. The results are shown in Table 3.

Reference Example 2

2-Pyrrolidone was added to commercially available 1,4-butanediol (manufactured by Mitsubishi Chemical Corporation) to prepare a 1,4-butanediol-containing composition containing 2-pyrrolidone in a concentration, as converted into a nitrogen atom, of 40.0 ppm by weight. 2.0 g of the 1,4-butanediol-containing composition was charged into a 9-mL glass vial, 1.2 mg of p-toluenesulfonic acid monohydrate was added, and the mixture was stirred at 60° C. for 2 hours.

As a result of analyzing the content of tetrahydrofuran after heating, it was found to be 1,100 ppm by weight. The results are shown in Table 3.

Reference Example 3

Procedures exactly the same as those in Reference Example 2 were carried out, except for using a 1,4-butanediol-containing composition containing 2-pyrrolidone in a concentration, as converted into a nitrogen atom, of 60.0 ppm by weight.

As a result of analyzing the content of tetrahydrofuran after heating, it was found to be 1,146 ppm by weight. The results are shown in Table 3.

Reference Example 4

Procedures exactly the same as those in Reference Example 2 were carried out, except for using a 1,4-butanediol-containing composition containing 2-pyrrolidone in a concentration, as converted into a nitrogen atom, of 80.0 ppm by weight.

As a result of analyzing the content of tetrahydrofuran after heating, it was found to be 1,290 ppm by weight. The results are shown in Table 3.

Reference Example 5

20.0 g of commercially available 1,4-butanediol (manufactured by Mitsubishi Chemical Corporation) was transferred into a 100-mL stainless steel autoclave provided with an inner cylinder made of TEFLON (a registered trademark), and 12 mg of p-toluenesulfonic acid monohydrate was added. The inside of the container was subjected to nitrogen substitution, followed by stirring at 140° C. for 2 hours.

As a result of analyzing the generation amount of tetrahydrofuran, it was found to be 6.7% by weight. The results are shown in Table 3.

Reference Example 6

Procedures exactly the same as those in Reference Example 5 were carried out, except for using a 1,4-butanediol-containing composition containing 2-pyrrolidone in a concentration, as converted into a nitrogen atom, of 40.0 ppm by weight in place of the commercially available 1,4-butanediol.

As a result of analyzing the content of tetrahydrofuran after heating, it was found to be 6.6% by weight. The results are shown in Table 3.

Reference Example 7

Procedures exactly the same as those in Reference Example 2 were carried out, except for using a 1,4-butanediol-containing composition containing ammonia in a concentration, as converted into a nitrogen atom, of 40.0 ppm by weight in place of the 2-pyrrolidone.

As a result of analyzing the content of tetrahydrofuran after heating, it was found to be 709 ppm by weight. The results are shown in Table 3.

Reference Example 8

Procedures exactly the same as those in Reference Example 2 were carried out, except for using a 1,4-butanediol-containing composition containing ammonia in a concentration, as converted into a nitrogen atom, of 60.0 ppm by weight in place of the 2-pyrrolidone.

As a result of analyzing the content of tetrahydrofuran after heating, it was found to be 614 ppm by weight. The results are shown in Table 3.

Reference Example 9

Procedures exactly the same as those in Reference Example 2 were carried out, except for using a 1,4-butanediol-containing composition containing ammonia in a concentration, as converted into a nitrogen atom, of 80.0 ppm by weight in place of the 2-pyrrolidone.

As a result of analyzing the content of tetrahydrofuran after heating, it was found to be 90 ppm by weight. The results are shown in Table 3.

Reference Example 10

Procedures exactly the same as those in Reference Example 5 were carried out, except for using a 1,4-butanediol-containing composition containing ammonia in a concentration, as converted into a nitrogen atom, of 40.0 ppm by weight in place of the commercially available 1,4-butanediol.

As a result of analyzing the content of tetrahydrofuran after heating, it was found to be 1.0% by weight. The results are shown in Table 3.

Example 13

In a 500-mL glass-made flask reactor provided with a glass-made cooling tube for distillation, 300.0 g of 1,4BG containing 2-pyrrolidone in a concentration, as converted into a nitrogen atom, of 10.0 ppm by weight was added, 1.50 g of p-toluenesulfonic acid (0.5% by weight relative to the reaction solution) was charged, and heating was carried out by using an oil bath such that the internal liquid temperature reached 145° C. After the internal liquid temperature was stabilized at 145° C., 265.8 g of a distillation liquid containing THF which had been condensed by the cooling tube was extracted into a glass-made storage vessel, thereby obtaining 34.2 g of a residual liquid (the amount of a by-product solid in the residual liquid: 2.8 mg) within the flask reactor. The results are shown in Table 4.

Comparative Example 5

The same procedures as those in Example 13 were carried out, except for using 1.4BG containing 2-pyrrolidone in a concentration, as converted into a nitrogen atom, of 0.1 ppm by weight in the raw material 1.4BG.

260.9 g of a distillation liquid containing THF was extracted into a glass-made storage vessel, thereby obtaining 34.7 g of a residual liquid (the amount of a by-product solid in the residual liquid: 42.0 mg) within the flask reactor. The results are shown in Table 4.

Comparative Example 6

The same procedures as those in Example 13 were carried out, except for using 1.4BG containing ammonia in a concentration, as converted into a nitrogen atom, of 10.0 ppm by weight in the raw material 1.4BG.

268.4 g of a distillate containing THF was extracted into a glass-made storage vessel, thereby obtaining 31.6 g of a residual liquid (the amount of by-product solid in the residual liquid: 67.1 mg) within the flask reactor. The results are shown in Table 4.

From Examples 1 to 9 and Comparative Examples 1 to 3, it is understood that the 1,4-butanediol-containing composition containing a specified amount of a nitrogen-containing compound according to the present invention is a 1,4BG-containing composition which is able to inhibit the generation amount of THT due to heating and when used as a raw material at the time of production of PBT, has high thermal stability.

In addition, it is understood that in comparison with Comparative Example 4, Examples 10 to 12 in which PBT is produced using the 1,4-butanediol-containing composition of the present invention are able to inhibit the degree of conversion into THF.

In addition, it is understood that Reference Examples 2 to 4 in which tetrahydrofuran is produced using the 1,4-butanediol-containing composition of the present invention are equal in terms of the amount of conversion into THF to Reference Example 1 and free from catalyst deterioration. On the other hand, it is understood that in Reference Examples 7 to 9 in which ammonia having high basicity is added, the amount of conversion into THF decreases with an increase of the amount of the nitrogen compound, and the catalyst is deteriorated. The same is also found even when the reaction temperature is increased as compared with Reference Examples 5, 6, and 10. Furthermore, from Example 13 and Comparative Examples 5 and 6, it is understood that when tetrahydrofuran is produced using the 1,4-butanediol-containing composition of the present invention, the formation of a solid can be inhibited.

TABLE 1

| | | 1,4-Butanediol-containing composition | | | | |
|---|---|---|---|---|---|---|
| | | Amide compound | | | Concentration | Formation amount |
| | Name | Structure | Content (ppm by weight) * | of 1,4-BG (% by weight) | pH | of THF (ppm by weight) |
| Example 1 | Acetamide | (structure: CH₃-C(=O)-NH₂) | 5 | 99.6 | 5.6 | 800 |
| Example 2 | 2-Pyrrolidone | (structure: 2-pyrrolidone) | 1.2 | 99.6 | 5.5 | 2998 |
| Example 3 | 2-Pyrrolidone | (structure: 2-pyrrolidone) | 5 | 99.6 | 5.5 | 2180 |

TABLE 1-continued

| | 1,4-Butanediol-containing composition | | | | | |
|---|---|---|---|---|---|---|
| | Amide compound | | | Concentration | | Formation amount |
| | Name | Structure | Content (ppm by weight) * | of 1,4-BG (% by weight) | pH | of THF (ppm by weight) |
| Example 4 | 2-Pyrrolidone | (structure) | 21 | 99.6 | 5.5 | 978 |
| Example 5 | 2-Pyrrolidone | (structure) | 50 | 99.6 | 5.5 | 2109 |
| Example 6 | N-Methylpyrrolidone | (structure) | 1.2 | 99.6 | 5.5 | 4020 |
| Example 7 | N-Methylpyrrolidone | (structure) | 5 | 99.6 | 5.5 | 1300 |
| Example 8 | N-Methylpyrrolidone | (structure) | 21 | 99.6 | 5.5 | 704 |
| Example 9 | N-Methylpyrrolidone | (structure) | 50 | 99.6 | 5.5 | 1335 |
| Comparative Example 1 | None | — | — (Not more than a detection limit) | 99.6 | 5.5 | 6800 |
| Comparative Example 2 | N-Methylpyrrolidone | (structure) | 0.5 | 99.6 | 5.5 | 12507 |
| Comparative Example 3 | 2-Pyrrolidone | (structure) | 0.1 | 99.6 | 5.5 | 7773 |

* Content as converted into a nitrogen atom

TABLE 2

| | Formed polymer | Content of amide compound (ppm by weight) * | Concentration of 1,4-BG in raw material 1,4-butanediol-containing composition (% by weight) | pH of raw material 1,4-butanediol-containing composition | Degree of conversion into THF (%) | Degree of coloration of formed polymer |
|---|---|---|---|---|---|---|
| Example 10 | PBT | 4 | 99.4 | 5.5 | 63.7 | 2.2 (color-b) |
| Example 11 | PBT | 6.6 | 99.4 | 5.5 | — | 2.9 (color-b) |
| Example 12 | PBT | 20.2 | 99.4 | 5.5 | 64.6 | 3.3 (color-b) |
| Comparative Example 4 | PBT | — (Not more than a detection limit) | 99.4 | 5.5 | 78.6 | — |

* Content as converted into a nitrogen atom

TABLE 3

| | 1,4-Butanediol-containing composition | | | | | |
|---|---|---|---|---|---|---|
| | Amide compound | | | Concentration | | Formation amount |
| | Name | Structure | Content (ppm by weight) *1 | of 1,4-BG (% by weight) | pH | of THF (ppm by weight) |
| Reference Example 1 | None | — | — (Not more than a detection limit) | 99.6 | 5.5 | 1103 |
| Reference Example 2 | 2-Pyrrolidone | 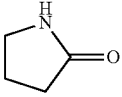 | 40 | 99.6 | 5.5 | 1100 |
| Reference Example 3 | 2-Pyrrolidone | 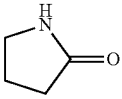 | 60 | 99.6 | 5.5 | 1146 |
| Reference Example 4 | 2-Pyrrolidone | 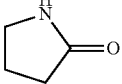 | 80 | 99.6 | 5.5 | 1290 |
| Reference Example 5 *2 | None | — | — (Not more than a detection limit) | 99.6 | 5.5 | 67000 |
| Reference Example 6 *2 | 2-Pyrrolidone | 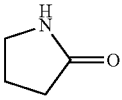 | 40 | 99.6 | 5.5 | 66000 |
| Reference Example 7 | Ammonia | NH₃ | 40 | 99.6 | 5.5 | 709 |
| Reference Example 8 | Ammonia | NH₃ | 60 | 99.6 | 5.5 | 614 |
| Reference Example 9 | Ammonia | NH₃ | 80 | 99.6 | 5.5 | 90 |
| Reference Example 10 | Ammonia | NH₃ | 40 | 99.6 | 5.5 | 10200 |

*1 Content as converted into a nitrogen atom;
*2 Reaction temperature: 140° C.

TABLE 4

| | Composition of raw material liquid | | | Reaction results | | | |
|---|---|---|---|---|---|---|---|
| | | Concentration of nitrogen | | Composition of distillation liquid | | | Formation |
| | Concentration of 1,4BG (% by weight) | (ppm by weight relative to raw material liquid) | Derived from nitrogen | Concentration of THF (% by weight) | Concentration of water (% by weight) | Yield of THF (%) | rate of THF (g/hr) |
| Example 13 | 99.7 | 10 | 2P | 80.0 | 19.6 | 88.8 | 61.2 |
| Comparative Example 5 | 99.7 | Not more than 0.1 | 2P | 78.8 | 19.9 | 86.3 | 87.5 |
| Comparative Example 6 | 99.7 | 10 | NH₃ (25% aqueous solution) | 78.9 | 19.6 | 88.1 | 68.0 |

TABLE 4-continued

| | | Reaction results | | | |
|---|---|---|---|---|---|
| | | Composition of residual liquid in reactor | | Yield of by-product solid (ppm by weight) | (Yield of by-product solid)/ (yield of THF) |
| | Distillation rate (%) | Concentration of nitrogen (ppm by weight) | Concentration of water (% by weight) | | |
| Example 13 | 88.6 | 87.7 | 5.8 | 3 | 3 |
| Comparative Example 5 | 88.4 | Not more than 0.1 | 1.7 | 47 | 54 |
| Comparative Example 6 | 89.5 | 0.5 | 7.9 | 67 | 76 |

While the invention has been described in detail and with reference to specific embodiments thereof, it will be apparent to one skilled in the art that various changes and modifications can be made therein without departing from the spirit and scope thereof. The present application is based on a Japanese patent application filed on Jul. 8, 2011 (Japanese Patent Application No. 2011-151716) and a Japanese patent application filed on Nov. 2, 2011 (Japanese Patent Application No. 2011-241572), the contents of which are incorporated herein by reference.

The invention claimed is:

1. A 1,4-butanediol-containing composition having a concentration of 1,4-butanediol of 99.00% by weight or more and not more than 99.99% by weight and containing 2-pyrrolidone or N-methylpyrrolidone in a concentration, as converted into a nitrogen atom, of from 1.0 to 25 ppm by weight, wherein the 1,4-butanediol-containing composition is used to produce tetrahydrofuran.

2. The 1,4-butanediol-containing composition according to claim 1, which has a pH is 5.0 or more and not more than 7.9.

3. The 1,4-butanediol-containing composition according to claim 1, which has a thermal stability as measured by the formation of tetrahydrofuran of not greater than about 2998 ppm by weight.

* * * * *